United States Patent [19]
Vassilev et al.

[11] Patent Number: 6,124,349
[45] Date of Patent: Sep. 26, 2000

[54] METHOD FOR PREPARATION OF PHARMACEUTICAL-GRADE DITHIOCARBAMATE

[75] Inventors: Vassil P. Vassilev; Wei-Cheng Liaw, both of San Diego; Ching-San Lai, Encinitas, all of Calif.

[73] Assignee: Medinox, Inc., San Diego, Calif.

[21] Appl. No.: 09/252,901

[22] Filed: Feb. 18, 1999

[51] Int. Cl.[7] .................................................. A01N 47/10
[52] U.S. Cl. ............................ 514/476; 564/74; 564/75
[58] Field of Search .............................. 514/476; 564/74, 564/75

[56] References Cited

U.S. PATENT DOCUMENTS

| | | | |
|---|---|---|---|
| 5,741,815 | 4/1998 | Lai | 514/492 |
| 5,747,532 | 5/1998 | Lai | 514/491 |
| 5,756,540 | 5/1998 | Lai | 514/492 |
| 5,847,004 | 12/1998 | Lai | 514/599 |

OTHER PUBLICATIONS

Lee et al., "Sugar-Linked Dithiocarbamates as Modulators of Metabolic and Genotoxic Properties of N-Nitroso Compounds," *J. Med. Chem.*, 37:3154–3162 (1994).

Shinobu, et al., "Sodium N-Methyl-D-glucamine Dithiocarbamate and Cadmium Intoxication," *Acta Pharmacol. et Toxicol.*, 54:189–194 (1984).

Singh et al., "Molecular-Modeling Design of Cadmium-Mobilizing Agents: A Novel Biscarbodithioate," *Chem. Res. Toxicol.*, 7:614–620 (1994).

*Primary Examiner*—Gary Geist
*Assistant Examiner*—Taylor V. Oh
*Attorney, Agent, or Firm*—Gray Cary Ware & Freidenrich LLP; Stephen E. Reiter; June M. Learn

[57] ABSTRACT

The present invention provides methods for producing pharmaceutical-grade particulate dithiocarbamates from secondary amines by vigorously contacting at least one secondary amine and a pharmaceutically acceptable diluent that is a solvent for the carbon disulfide, but not for the secondary amine in an inert gas atmosphere, cooling the mixture so as to precipitate the dithiocarbamate therefrom, and separating the precipitated dithiocarbamate from the cooled mixture. The preferred solvent contains absolute ethanol. In alternative embodiments, the invention further provides methods for purifying a dithiocarbamate to obtain a pharmaceutical-grade dithiocarbamate particulate from a dithiocarbamate feed and methods for producing a sterile pharmaceutical-grade dithiocarbamate from a dithiocarbamate feed.

72 Claims, 5 Drawing Sheets

METHOD FOR PREPARATION OF PHARMACEUTICAL-GRADE DITHIOCARBAMATE

FIELD OF THE INVENTION

The present invention relates to methods for synthesis of dithiocarbamates. More particularly, the present invention relates to methods for producing pharmaceutical-grade dithiocarbamates.

BACKGROUND OF THE INVENTION

Dithiocarbamates have been found to have numerous pharmaceutical utilities, for example as nitric oxide scavengers for the treatment of inflammatory and infectious diseases (See, for example, the recent work of Lai, as described in U.S. Pat. Nos. 5,714,815, 5,756,540, 5,757,532, and 5,847,004, the contents of each of which are hereby incorporated by reference in their entirety). Prior to the discovery of pharmaceutical utilities for dithiocarbamates, more traditional uses thereof include use in chemical or commercial endeavors, for example, for precipitating metals in chemical analysis or for synthesis of heterocyclic compounds (Thorn & Ludwig, *The Dithiocarbamates and Related Compounds*, Elsevier, Amsterdam, 1962, pages 61–126). These more traditional uses typically do not require the attributes most desired for pharmaceutical-grade dithiocarbamates, such as sterility, purity and stable, fine particulate form. The traditional methods of synthesizing dithiocarbamates are, therefore, unsuitable for preparation of pharmaceutical-grade dithiocarbamates.

The chemical nature of dithiocarbamates, which are unstable under acidic conditions, requires their preparation to be accomplished as organic or inorganic salts (Thorn & Ludwig, pages 7–42). One synthetic method for producing dithiocarbamates utilizes an organic amine, which is used in excess. However, organic amines are relatively expensive, making the production cost high. In addition, the presence of organic amine may render the resulting product dithiocarbamate unsuitable for pharmaceutical uses.

An alternative synthetic method designed to avoid use of organic amines produces the dithiocarbamate in the form of an alkali metal salt, such as a sodium salt. Since sodium salts are generally soluble in water, the solvent of choice in the preparation of dithiocarbamates by the alkali metal salt method is water (H. Xian et al., *Hangzhou Daxue Xuebao, Ziran Kexueban*, 9:81–84, 1982 (*Chemical Abstracts* 97:23417, 1982). However, side products are produced during the synthesis reaction at higher temperature, requiring the temperature of the synthesis reaction to be controlled to a temperature of no greater than about 20° C. up to about 30° C. to avoid undesirable side products. Therefore, the reaction temperature is usually controlled to between –5° C. and 10° C. (B. H. Lee et al., *J. Med. Chem.* 37:3154–3162, 1994).

To obtain the dithiocarbamate product in a stable solid form, organic solvent is frequently used to initiate the precipitation of the end product from the reaction mixture. Generally, methanol, acetone, or a mixture of methanol and ethanol are used as the solvent for this purpose (L. A. Shinobu et al., *Acta Pharm. Toxicol.* 54:189–194, 1984; P. K. Singh et al., *Chem. Res. Toxicol.* 7:614–620, 1994). However, methanol and acetone are toxic if ingested, rendering the products produced by this method unsuitable for use as a pharmaceutical.

Despite the knowledge in the art regarding methods for producing dithiocarbamates, there is a need for new and better methods for producing pharmaceutical-grade and/or sterile dithiocarbamates as a finely divided particulate.

SUMMARY OF THE INVENTION

In accordance with the present invention, there are provided methods for producing pharmaceutical-grade dithiocarbamates. Invention methods are preferably conducted under sterile conditions, thereby producing a sterile pharmaceutical-grade dithiocarbamate. In one embodiment, the invention method comprises vigorously contacting a mixture of carbon disulfide, at least one secondary amine, and a pharmaceutically acceptable diluent in a mixing zone under an inert gas atmosphere, wherein the diluent is a solvent for the carbon disulfide, but not for the dithiocarbamate. The invention method further comprises cooling the mixture so as to precipitate the dithiocarbamate therefrom, and separating the precipitated dithiocarbamate from the cooled mixture. Preferably, the diluent comprises ethanol.

In another embodiment, the invention synthesis method comprises vigorously contacting a mixture of carbon disulfide, at least one secondary amine and a pharmaceutically acceptable diluent that is a solvent for the carbon disulfide, but not for the dithiocarbamate, in a mixing zone under an inert gas atmosphere and under conditions suitable for precipitating the dithiocarbamate. The invention synthesis method further comprises separating the precipitated dithiocarbamate from the mixture. The diluent generally comprises ethanol. The carbon disulfide can also be introduced into the mixing zone as a liquid, for example as a solution in ethanol. The secondary amine can optionally be introduced into the mixing zone as an alkaline aqueous solution.

The invention method optionally further comprises vigorously stirring a solution of the precipitated dithiocarbamate in pharmaceutical-grade water in a second mixing zone, while adding pharmaceutical-grade ethanol thereto under conditions suitable for forming a suspension containing a finely-divided dithiocarbamate precipitate therein, and separating the finely divided dithiocarbamate precipitate from the suspension, for example, by filtration or other suitable means.

In the present invention, there are also provided method (s) for obtaining pharmaceutical-grade dithiocarbamate from a dithiocarbamate. In this embodiment, the invention method comprises vigorously stirring a solution of dithiocarbamate in pharmaceutical-grade water, while adding pharmaceutical-grade ethanol thereto under conditions suitable for forming a suspension containing a finely-divided dithiocarbamate precipitate therein, and separating the dithiocarbamate precipitate from the suspension. The finely divided dithiocarbamate precipitate is preferably washed with ethanol having an ethanol content in the range from about 70% ethanol to absolute ethanol to obtain the pharmaceutical-grade dithiocarbamate.

The accordance with present invention further provides method(s) for producing sterile pharmaceutical-grade dithiocarbamates. In this embodiment, the invention method comprises sterilizing a solution of dithiocarbamate in pharmaceutical-grade water, vigorously stirring the solution in a sterile mixing zone while adding thereto sterile pharmaceutical-grade ethanol under conditions suitable for forming a suspension containing a finely-divided dithiocarbamate precipitate therein, and separating the dithiocarbamate precipitate from the suspension under sterile conditions. The aqueous solution of dithiocarbamate and the ethanol can be sterilized by passage into the mixing zone through sterilizing filters.

DESCRIPTION OF THE SPECIFIC EMBODIMENTS

In accordance with the present invention, there are provided methods for producing pharmaceutical-grade dithiocarbamates. A sterile filter is represented by an open circle. Invention methods are preferably conducted under sterile conditions, thereby producing a sterile pharmaceutical-grade dithiocarbamate.

In one embodiment, the invention method comprises vigorously contacting a mixture of carbon disulfide, at least one secondary amine, and a pharmaceutically acceptable diluent that is a solvent for the carbon disulfide, but not for the dithiocarbamate, in a mixing zone under an inert gas atmosphere and under conditions suitable for precipitating the dithiocarbamate. Invention method further comprises separating the precipitated dithiocarbamate from the mixture. The invention methods for producing a pharmaceutically acceptable dithiocarbamate can be performed either as a continuous process or as a batch process.

Among the secondary amines suitable for use in preparation of pharmaceutically acceptable dithiocarbamates are those having the formula $R_1R_2NH$, wherein each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate molecules, thereby linking said molecules together so as to form a bis(dithiocarbamate) species, and the like, and suitable combinations thereof.

For example, the secondary amine can have the formula $R_1R_2NH$, wherein each of $R_1$ and $R_2$ is a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl. For example $R_1$ can be a $C_2$ up to $C_8$ alkyl or substituted alkyl, wherein the substituents are carboxyl, acetyl, pyridinyl, pyrrolidinyl, amino, amido, hydroxy or nitro, and $R_2$ is either $C_1$ up to $C_6$ alkyl or substituted alkyl, or $R_2$ can cooperate with $R_1$ to form a 5-, 6- or 7-membered ring including N, $R_2$ and $R_1$. In the secondary amines presently preferred for use in the practice of invention method(s) for the preparation of dithiocarbamates, $R_1$ is a $C_2$ up to $C_8$ alkyl or substituted alkyl, and wherein the substituents are selected from carboxyl, acetyl, amido or hydroxy, and $R_2$ is a $C_1$ up to $C_4$ alkyl or substituted alkyl. The secondary amines are preferably introduced into the mixing zone as an alkaline aqueous solution.

To avoid contamination of the dithiocarbamate product with a solvent that is not pharmaceutically acceptable and to assist in precipitation of the dithiocarbamate from the reaction mixture as a stable solid, the diluent generally comprises ethanol and excludes such pharmaceutically inappropriate solvents as methanol or acetone. For example, the ethanol and the carbon disulfide can be introduced into the mixing zone together as a solution of carbon disulfide in ethanol, for example in absolute ethanol. The diluent can further contain water and a suitable cation, such as sodium, for formation of a dithiocarbamate salt. Since alkali metal salts of dithiocarbamates are soluble in water, it is preferred that the cation be an alkali metal cation.

In a preferred embodiment of the invention method for producing a pharmaceutically acceptable dithiocarbamate, the carbon disulfide is added to the reaction mixture dissolved in an aqueous solution of sodium hydroxide. Alternatively, the secondary amine can be introduced into the mixing zone as an alkaline aqueous solution.

The carbon disulfide and the secondary amine are vigorously contacted in the mixing zone in the invention methods. The vigorous contacting can include any means known in the art, such as centrifugation, mixing, stirring, sparging, vigorous bubbling of an inert gas through the reaction mixture, and the like, or a combination of any two or more thereof. For example, the mixing can be accomplished by any magnetic or mechanical stirring device capable of vigorously stirring the slurry formed by precipitation of the dithiocarbamate in the reaction zone. In one embodiment, the stirring device is magnetic and the speed of the stirring device is from about 10 rpm to about 200 rpm.

Generally, the conditions suitable for precipitating the dithiocarbamate include cooling the reaction mixture, preferably to a temperature of from about minus 10° C. to about 20° C. at atmospheric pressure. The cooling of the reaction mixture can be accomplished by any method known in the art, including, but not limited to, submerging a reaction vessel containing the mixture in an ice water or ice/salt water bath. Alternatively, the reaction vessel can be refrigerated using known technologies.

The conditions suitable for precipitation of the dithiocarbamate from the reaction mixture optionally further include subjecting the reaction mixture to a reduced pressure (i.e., reduced with respect to the pressure in the mixing zone), for example, by passing the reaction mixture through a separation zone, such as a separation vessel, that can be maintained at a reduced pressure.

When prepared according to the invention methods, the dithiocarbamate is in the form of a particulate solid, preferably a finely divided particulate solid having a major dimension in the size range from about 100 $\mu$m to about 1 cm, or smaller. Separation of the particulate dithiocarbamate from the reaction mixture can also be enhanced by passage of the reaction mixture through a filter, a screen, or a combination thereof so as to collect the dithiocarbamate as a filter cake. A screen or filter having a pore size generally in the range from about 0.1 $\mu$m to about 50 $\mu$m, for example, typically in the range from about 10 $\mu$m to about 50 $\mu$m, and preferably in the range from about 10 $\mu$m to about 20 $\mu$m, is particularly useful for obtaining a finely divided dithiocarbamate product with pharmaceutical utility.

The invention method for preparing a pharmaceutical-grade dithiocarbamate optionally further comprises washing the precipitated dithiocarbamate with ethanol having an ethanol content in the range from about 70% ethanol to absolute ethanol. For example, during the washing, the ethanol content can be increased from about 70% ethanol to absolute ethanol, with the increase being made gradually or in incremental steps.

In another embodiment of the invention methods for producing a pharmaceutically acceptable dithiocarbamate, the method may also further comprise introducing into the reaction zone an inert gas, such as nitrogen, argon, and the like, or a combination thereof. For example, the inert gas can be introduced into the mixing zone at a flow rate generally from about 0.1 liters to about 300 liters per minute, typically flow rates fall in the range of about 30 liters to about 100 liters per minute, or from about 0.1 liter to about 50 liters per minute, with flow rates of from about 1.0 liter to about 20 liters per minute being the presently preferred flow rates. The mixing zone is optionally substantially closed to facilitate use of the inert purge gas.

Figure 1:
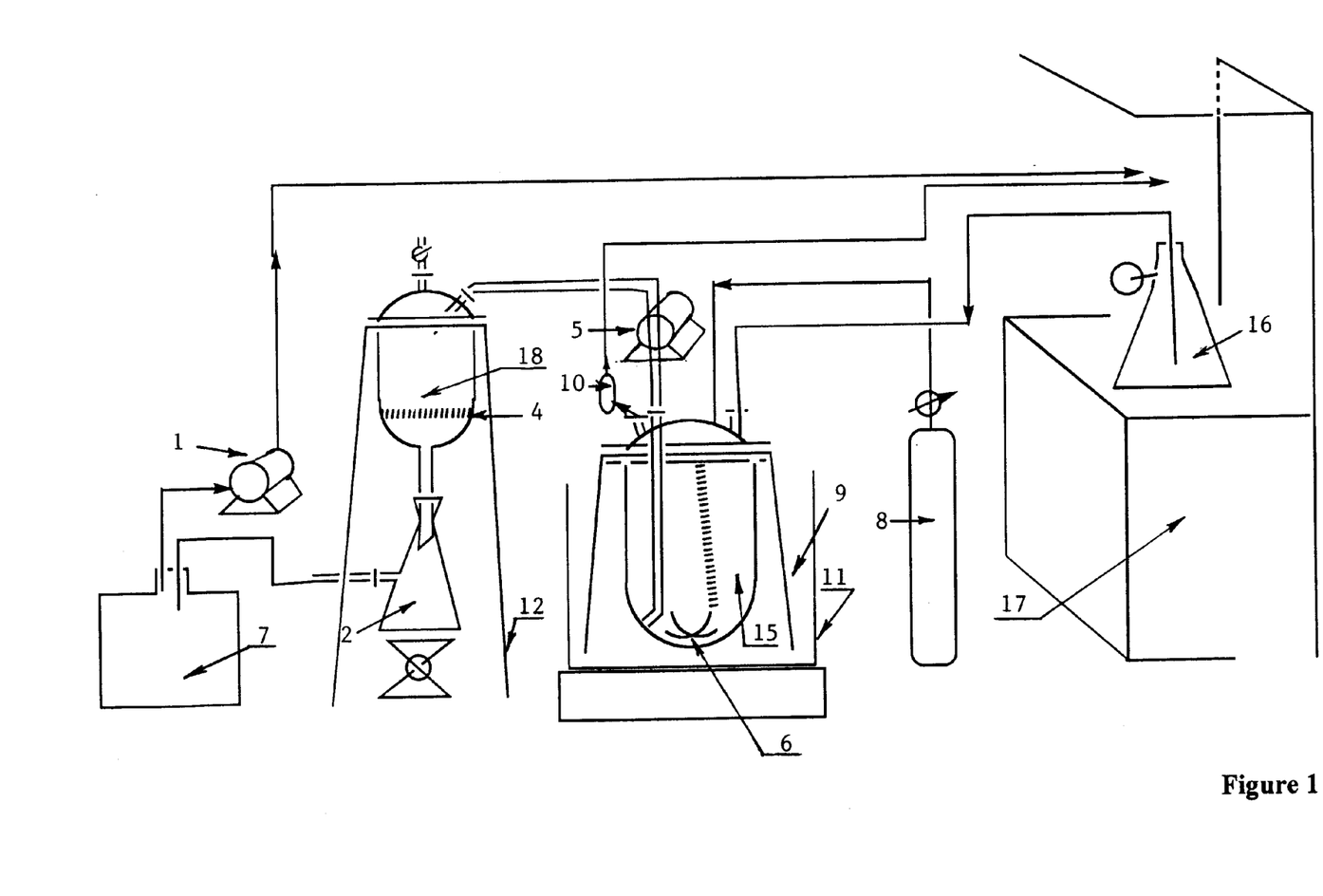
FIG. 1 is a schematic diagram illustrating the invention method for producing a pharmaceutical-grade dithiocarbamate from carbon disulfide dissolved in ethanol and a secondary amine. An aqueous solution of the secondary amine and a solution of carbon disulfide in absolute ethanol is fed into a reaction vessel submerged in an ice bath and continuously stirred. Precipitated dithiocarbamate product is separated from the reaction mixture in a separation vessel by passage through a glass filter while waste filtrate is collected.

The invention dithiocarbamate synthesis method is further illustrated in Step I of the Example below and by FIG. 1, which is a schematic diagram illustrating a bench scale process and equipment for producing pharmaceutical-grade dithiocarbamate according to the invention synthesis method. As shown in FIG. 1, the secondary amine dissolved in water is maintained under hood 17 until loaded into reaction vessel 15. A solution of carbon disulfide in absolute ethanol is transferred by siphoning from feed holder 16 to reaction vessel 15. The reaction mixture in the reaction vessel is vigorously stirred by stirrer 6 and cooled by submersion of reaction vessel 15 into cooling bath 9, which contains a slurry of water and ice. The reaction vessel is continuously blanketed with nitrogen gas from purge gas source 8 fed through gas bubbler 10. The reaction mixture, which contains purge gas and precipitated dithiocarbamate product, is pumped from the reaction vessel via peristaltic pump 5 into separation vessel 18. In separation vessel 18, which is maintained under reduced pressure by vacuum pump 1, the precipitated dithiocarbamate is separated from the reaction mixture by passage through glass filter 4 while the waste filtrate passes into filtering flask 2 with overflow into waste container 7. The purge gas is drawn off from waste container 7 through vacuum pump 1 to hood 17.

In an alternative embodiment, the invention method further comprises a purification step to further purify the dithiocarbamate synthesized as described above by the invention synthesis method(s). In this embodiment, the invention synthesis method further comprises vigorously stirring in a second mixing zone a solution of the precipitated dithiocarbamate in pharmaceutical-grade water while adding pharmaceutical-grade ethanol thereto under conditions suitable for forming a suspension containing a finely-divided dithiocarbamate precipitate therein, and separating the finely divided dithiocarbamate precipitate from the suspension. Dissolving the precipitate in pharmaceutical-grade water and contacting the solution with a pharmaceutical-grade ethanol, preferably absolute ethanol, aids in obtaining a sterile product and eliminates undesirable by products from the precipitate dithiocarbamate.

Alternatively, this purification step can be performed independently of the above described method for producing a pharmaceutical-grade dithiocarbamate by using any particulate dithiocarbamate as the feed. When performed independently, the invention purification method comprises vigorously stirring in a mixing zone a solution of a dithiocarbamate in pharmaceutical-grade water while adding pharmaceutical-grade ethanol thereto under conditions suitable for forming a suspension containing a finely-divided dithiocarbamate precipitate therein, and separating the finely divided dithiocarbamate precipitate from the suspension.

Among the dithiocarbamate feeds suitable for use in the invention purification methods are those having the structure (I) as follows:

wherein:

each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, cycloalkylene, substituted cycloalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, x is 1 or 2 and M is a suitable counterion, and the like, and suitable combinations thereof.

Presently preferred dithiocarbamate compounds having generic structure I are those wherein:

$R_1$ and/or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species.

Additional preferred dithiocarbamate compounds having generic structure I are those wherein:

$R_1$ and/or $R_2$ is a polyvalent moiety, wherein said polyvalent moiety serves as the same substituent for a plurality of dithiocarbamate structures, thereby linking said structures together so as to form a poly (dithiocarbamate) species.

Still further preferred dithiocarbamate compounds having generic structure I are those wherein:

each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, and $M=Fe^{+2}$ or $Fe^{+3}$.

Additional preferred dithiocarbamate compounds having generic structure I are those wherein:

$R_1$ is selected from a $C_2$ up to $C_8$ alkyl or substituted alkyl, wherein the substituents are selected from carboxyl, acetyl, pyridinyl, pyrrolidinyl, amino, amido, hydroxy or nitro, and $R_2$ is selected from a $C_1$ up to $C_8$ alkyl or substituted alkyl, and $M=Fe^{+2}$.

Still further preferred dithiocarbamate compounds having generic structure I are those wherein:

$R_1$ is selected from a $C_2$ up to $C_6$ alkyl or substituted alkyl, wherein the substituents are selected from carboxyl, acetyl, amido or hydroxy, and $R_2$ is selected from a $C_1$ up to $C_6$ alkyl or substituted alkyl, and $M=Fe^{+2}$.

Monovalent cations contemplated by structure I include $H^+$, $Na^+$, $NH_4^+$, tetraalkyl ammonium, and the like, although those of skill in the art recognize that H+is generally not preferred because of the relative instability of the resulting dithiocarbamate in aqueous media. Physiologically compatible divalent or trivalent transition metal cations contemplated by structure include charged forms of iron, cobalt, copper, manganese, ruthenium, or the like (e.g., $Fe^{+2}$, $Fe^{+3}$, $Co^{+2}$, $Co^{+3}$, $Cu^{+2}$, $Mn^{+2}$, $Mn^{+3}$ or $Ru^{+3}$). In accordance with the present invention, the ratio of dithiocarbamate-species to counter-ion M can vary widely. Thus, dithiocarbamates having no metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) are contemplated.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, dithiocarbamoyl, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "cycloalkylene" refers to divalent ring-containing groups containing in the range of about 3 up to 8 carbon atoms, and "substituted cycloalkylene" refers to cycloalkylene groups further bearing one or more substituents as set forth above.

As employed herein, "alkylene" refers to saturated, divalent straight or branched chain hydrocarbyl groups typically having in the range of about 2 up to 12 carbon atoms, and "substituted alkylene" refers to alkylene groups further bearing one or more substituents as set forth above.

As employed herein, "alkenyl" refers to straight or branched chain hydrocarbyl groups having at least one carbon—carbon double bond, and having in the range of about 2 up to 12 carbon atoms, and "substituted alkenyl" refers to alkenyl groups further bearing one or more substituents as set forth above.

As employed herein, "alkenylene" refers to divalent straight or branched chain hydrocarbyl groups having at least one carbon—carbon double bond, and typically having in the range of about 2 up to 12 carbon atoms, and "substituted alkenylene" refers to alkenylene groups further bearing one or more substituents as set forth above.

As employed herein, "alkynyl" refers to straight or branched chain hydrocarbyl groups having at least one carbon—carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "arylene" refers to divalent aromatic groups typically having in the range of 6 up to 14 carbon atoms and "substituted arylene" refers to arylene groups further bearing one or more substituents as set forth above.

As employed herein, "alkarylene" refers to alkyl-substituted divalent aryl groups typically having in the range of about 7 up to 16 carbon atoms and "substituted alkarylene" refers to alkarylene groups further bearing one or more substituents as set forth above.

As employed herein, "aralkylene" refers to aryl-substituted divalent alkyl groups typically having in the range of about 7 up to 16 carbon atoms and "substituted aralkylene" refers to aralkylene groups further bearing one or more substituents as set forth above.

As employed herein, "aralkenylene" refers to aryl-substituted divalent alkenyl groups typically having in the range of about 8 up to 16 carbon atoms and "substituted aralkenylene" refers to aralkenylene groups further bearing one or more substituents as set forth above.

As employed herein, "aralkynylene" refers to aryl-substituted divalent alkynyl groups typically having in the range of about 8 up to 16 carbon atoms and "substituted aralkynylene" refers to aralkynylene groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "heterocycloalkylene" refers to divalent cyclic (i.e., ring-containing) groups containing one or more heteroatoms (e.g., N, O, S, or the like) as part of the ring structure, and having in the range of 3 up to 14 carbon atoms and "substituted heterocycloalkylene" refers to heterocycloalkylene groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "acyl" refers to alkyl-carbonyl species.

As employed herein, "halogen" refers to fluoride, chloride, bromide or iodide atoms.

The stirring (under conditions suitable for forming a suspension containing a finely divided dithiocarbamate precipitate) and the separating at reduced pressure utilize generally the same techniques as discussed above with respect to the invention synthesis method(s) for producing a pharmaceutical-grade dithiocarbamate. The invention purification method and/or purification step in the synthesis method are illustrated in Step II of the Example below.

In another embodiment, there are provided method(s) for producing sterile dithiocarbamates. This embodiment comprises stirring a solution of dithiocarbamate in pharmaceutical-grade water, vigorously stirring the solution in a sterile mixing zone while adding thereto sterile pharmaceutical-grade ethanol under conditions suitable for forming a suspension containing a finely-divided dithiocarbamate precipitate therein, and separating the dithiocarbamate precipitate from the suspension at reduced pressure and under sterile conditions.

In practice of the invention method for obtaining sterile pharmaceutical-grade dithiocarbamates, the separating can involve passage of the precipitate through a separation zone maintained at reduced pressure. The separation can further involve passage of the suspension containing the precipitate (e.g. in the separation zone) through a filter, a screen, or a combination thereof, as described above with respect to the invention synthesis methods.

The method for producing sterile dithiocarbamate can further comprise washing the separated precipitate, for example, in the separation zone, with a sterile wash ethanol having an ethanol content in the range from about 70% ethanol to absolute ethanol. In one embodiment, during the washing the ethanol content in the wash ethanol is increased from about 70% ethanol to absolute ethanol, for example, either gradually or in one or more incremental steps. The wash ethanol aids in sterilizing and drying the dithiocarbamate product.

To further aid in obtaining a sterile product, each of the solution of dithiocarbamate and the ethanol can be sterilized by passage into the mixing zone through a sterilizing filter, such as is known in the art, for example, membrane filters of mixed cellulose esters and polysulphones (Millipore, Bedford, Mass.). Such sterilizing filters generally have pore sizes small enough to prohibit passage of microbes through the filter while allowing passage of dissolved small molecules, such as ethanol and the dithiocarbamates disclosed herein, for example pore sizes in the range of about 0.2 $\mu$m to about 75 $\mu$m are typical. The wash ethanol can also be sterilized by passage into the separation zone through such a sterilizing filter.

The invention method for producing sterile dithiocarbamate can further comprise drying the separated precipitate to constant weight, for example by passage of a sterile inert gas over the separated precipitate in a separation zone. The inert gas can be made sterile by passage into the separation zone through a sterilizing filter.

The invention method for producing sterile dithiocarbamate can also further comprise aseptic transfer, for example in a Class 100 sterile room, of a unit dose of the dried sterile dithiocarbamate into individual sterile vials. Usually, a unit dose of the pharmaceutical-grade dithiocarbamate is in the range from about 100 mg to about 10 grams, with typical unit doses following in the range of about 200 mg to about 3 grams.

Figure 2:
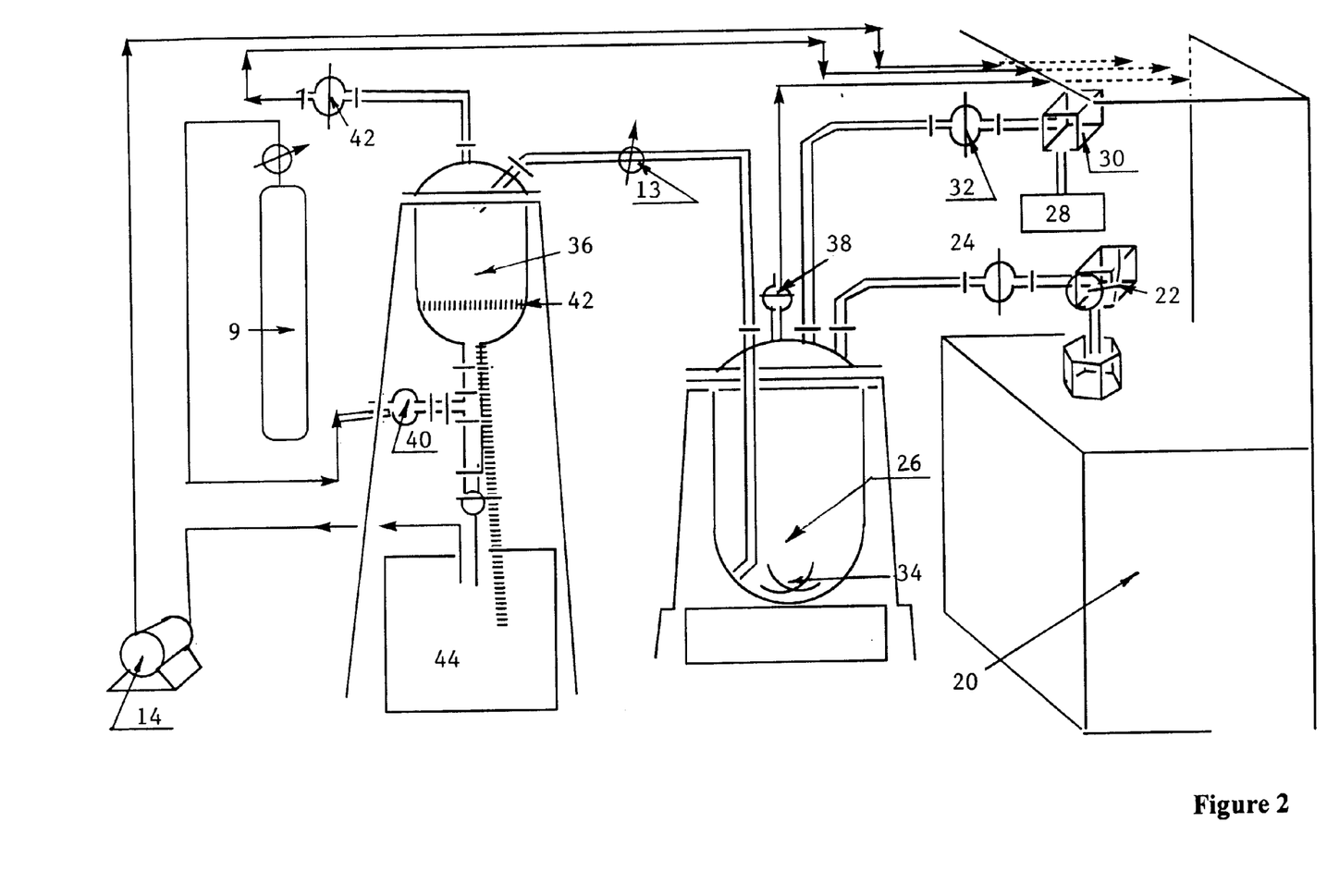
FIG. 2 is a schematic diagram illustrating the invention method for producing a sterile pharmaceutical-grade dithiocarbamate from an aqueous solution of a dithiocarbamate, such as is produced in the process illustrated in FIG. 1 herein. Feed streams of pharmaceutical-grade ethanol and a solution of dithiocarbamate in pharmaceutical-grade water are pumped into a reaction vessel under constant stirring. The dithiocarbamate precipitated in the reaction vessel is separated from the reaction mixture by passage into a separation vessel flushed by nitrogen gas. The feed streams of ethanol and of dithiocarbamate solution as well, as the nitrogen gas stream, are each sterilized by passage through a sterilizing filter to yield a sterile pharmaceutical-grade dithiocarbamate product.
Figure 5:
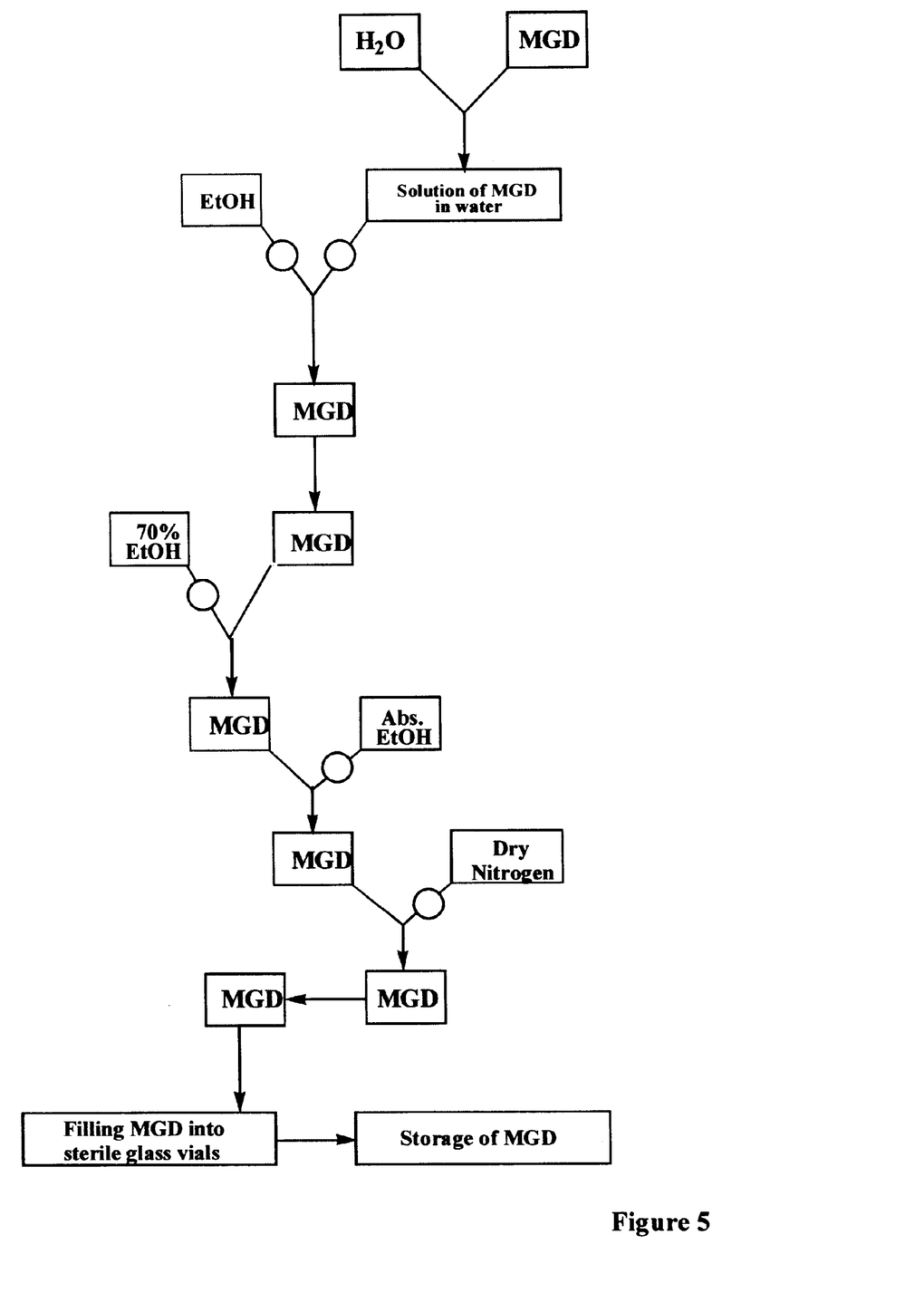
FIG. 5 is a schematic flow diagram illustrating an embodiment of the invention method for preparing a sterile pharmaceutical-grade dithiocarbamate. A sterile filter is represented by an open circle.

The invention method for producing a sterile pharmaceutical-grade dithiocarbamate is further illustrated in Step III of Example 1 below and by FIGS. 2 and 5, which illustrate, respectively, a bench scale process and equipment, and a schematic flow diagram, for producing sterile dithiocarbamate according to an embodiment of the invention wherein sterilizing filters are used to sterilize the dithiocarbamate solution feed, the ethanol feed, and the inert gases. In the embodiment illustrated in FIG. 2, a dithiocarbamate feed is dissolved in pharmaceutical-grade water and maintained under ventilated hood 20. From hood 20 the aqueous solution of dithiocarbamate is pumped via peristaltic pump 22 through a sterilizing filter 24 into reaction vessel 26. Meanwhile ethanol is pumped into reaction vessel 26 from ethanol source 28 via peristaltic pump 30, sterilizing filter 32, and silicon tubing 2. The reaction mixture in vessel 26 is vigorously mixed by stirrer 34 and then passed to separation vessel 36 through valve 13. In separation vessel 36, which is maintained under reduced pressure provided by vacuum pump 14 and flushed by nitrogen gas from gas source 9, the suspended particulate dithiocarbamate is collected from the reaction mixture by passage of the reaction mixture through glass filter 42.

The invention will now be described in greater detail by reference to the following non-limiting example.

EXAMPLE

Preparation of pharmaceutical-grade dithiocarbamate from N-methyl-D-glucamine (NMG)

Figure 3:
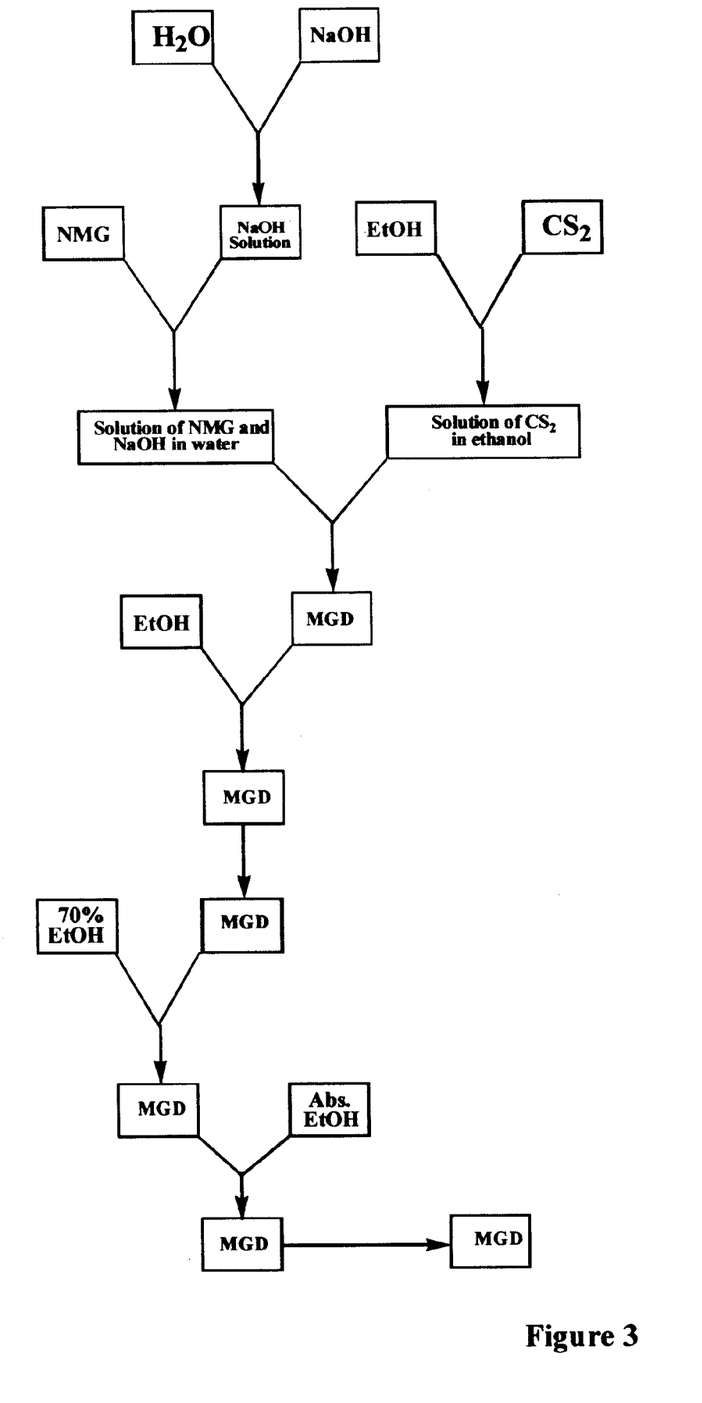
FIG. 3 is a schematic flow diagram illustrating an embodiment of the invention method for preparing pharmaceutical-grade dithiocarbamate from a secondary amine.

Part I: synthesis of N-methyl-D-glucamine dithiocarbamate (MGD). Pharmaceutical-grade MGD was prepared using the process illustrated in FIG. 1 according to the schematic process flow chart shown in FIG. 3 herein. A solution containing 0.6 kg of sodium hydroxide dissolved in 7.5 liters of water for injection (WFI) was prepared and injected into a 27 liter reaction vessel (FIG. 1). The sodium hydroxide solution in the reaction vessel was cooled to room temperature with an ice/salt bath, and then 3 kg of N-methyl-D-glucamine (NMG) was added to the alkaline solution and dissolved with stirring, making a solution having a 1:1 ratio of NMG to NaOH. Cooling of the solution was continued to a temperature of −10 C to 10° C. The reaction vessel was purged with nitrogen gas and kept under a constant nitrogen atmosphere during the remainder of the synthesis process.

A separate solution of 1.5 liters of carbon disulfide in 4.5 liters of absolute ethanol was prepared and cooled to −10° C. to 10° C. The cold solution of carbon disulfide was slowly added into the cold solution of NMG in NaOH in the reaction vessel with stirring over a period of about 20 to 25 minutes. Cooling and stirring of the reaction mixture was continued for an additional 20 minutes after all of the solution of $CS_2$ had been introduced into the reaction vessel. Then 15 liters of ethanol was introduced into the reaction vessel and stirring was continued for an additional two hours. To obtain the product dithiocarbamate as a solid, the reaction mixture containing the MGD precipitate was passed through a filter for collection while a vacuum suction was applied across the filter and while the filter cake was washed with wash ethanol having a progressively higher ethanol content: first, with 5 liters of 70% ethanol, then with 10 liters of 95% ethanol, and then with 4 liters of absolute ethanol. To dry the collected solid, the vacuum was maintained for three hours, and then the MGD was air dried to assure desiccation.

Figure 4:
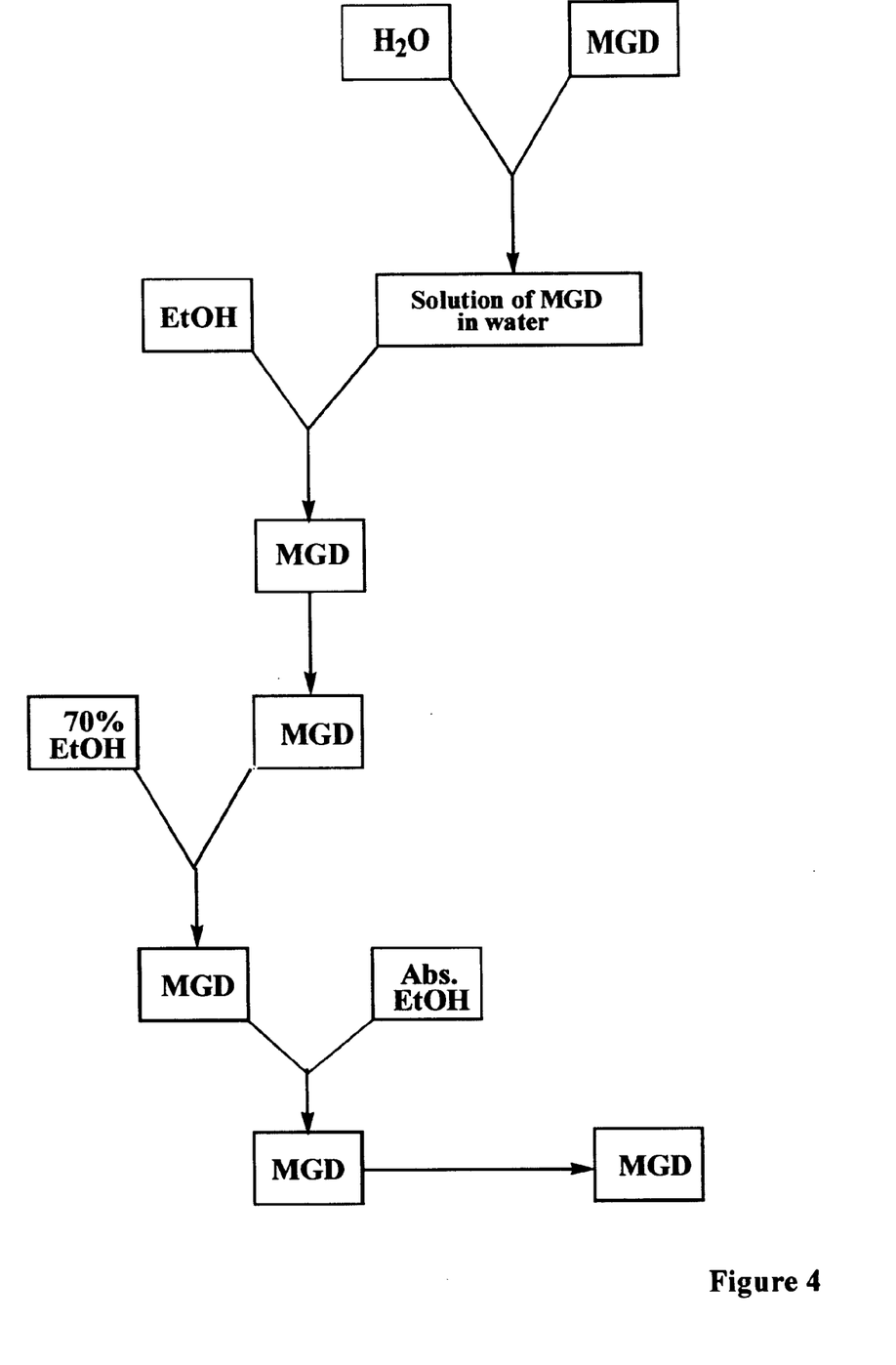
FIG. 4 is a schematic flow diagram illustrating an embodiment of the invention method for purifying a dithiocarbamate to obtain a pharmaceutical-grade dithiocarbamate.

Part II: Purification of MGD. The MGD prepared in Part I above was purified using the process illustrated in FIG. 1 according to the schematic process flow chart shown in FIG. 4 herein. MGD was transferred into a clean reaction vessel and dissolved in up to 8 liters of WFI. To precipitate the MGD as a solid, 19 liters of 95% ethanol were added with continuous stirring for another 25 minutes. The precipitated MGD was then passed through a filter for collection while a vacuum suction was applied across the filter and while the filter cake was washed with progressively purer ethanol: first with 5 liters of 70% ethanol, then with 10 liters of 95% ethanol, and then with 4 liters of absolute ethanol. To dry the collected solid, the vacuum was maintained for three hours, and then the MGD was air dried to assure desiccation.

Part III: Sterilization of MGD. The MGD prepared in Part II above was sterilized using the process illustrated in FIG. 2 according to the schematic process flow chart shown in FIG. 5 herein. The purified MGD was dissolved in up to 7 liters of water and delivered through a sterilizing filter having a pore size of 0.2 μm into a sterile precipitation vessel (FIG. 2). To precipitate the MGD, up to 20 liters of 95% ethanol was delivered into the sterile precipitation vessel through a sterilizing filter having a pore size of 0.2 μm. Then the precipitated MGD was filtered through a glass filter having a pore size of 50 to 75 μm while the filter cake was washed under vacuum as in Parts I and II above, except that the ethanol was delivered into the precipitation/filtration system through a sterilizing filter having a pore size of 0.2 μm. The filter cake of precipitated sterile MGD was dried to a constant weight (to assure complete desiccation) by applying a flow of nitrogen gas through a sterilizing filter. The yield was 2.4 kg of sterile, pharmaceutical-grade MGD.

The dried MGD was transferred under sterile conditions into a Class 100 sterile room for aseptic transfer of a unit dose (100 mg to 10 grams) into individual sterile glass vials and stored at room temperature.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A method for producing substantially methanol-free pharmaceutical-grade dithiocarbamate, said method comprising:

vigorously contacting a mixture of carbon disulfide, at least one secondary amine and a pharmaceutically acceptable, methanol-free diluent in a mixing zone under an inert gas atmosphere, wherein the diluent is a solvent for the carbon disulfide, but not for the dithiocarbamate, cooling the mixture so as to precipitate the dithiocarbamate therefrom, and separating the precipitated dithiocarbamate from the cooled mixture, wherein the dithiocarbamate precipitate is substantially methanol-free.

2. The method according to claim 1 wherein the diluent comprises ethanol.

3. The method according to claim 2 wherein the ethanol and the carbon disulfide are introduced into the mixing zone together as a solution of carbon disulfide in ethanol.

4. The method according to claim 1 wherein the secondary amine is introduced into the mixing zone as an alkaline aqueous solution.

5. The method according to claim 1 wherein the method is performed under sterile conditions.

6. A method for producing substantially methanol-free pharmaceutical-grade dithiocarbamate, said method comprising:

vigorously contacting a mixture of carbon disulfide, at least one secondary amine and a pharmaceutically acceptable, methanol-free diluent that is a solvent for the carbon disulfide, but not for the dithiocarbamate, in a mixing zone under an inert gas atmosphere and under conditions suitable for precipitating the dithiocarbamate, and separating the precipitated dithiocarbamate from the mixture, wherein the dithiocarbamate precipitate is substantially methanol-free.

7. The method according to claim 6 wherein the carbon disulfide is introduced into the mixing zone as a liquid.

8. The method according to claim 6 wherein the diluent comprises ethanol.

9. The method according to claim 8 wherein the ethanol is absolute ethanol.

10. The method according to claim 8 wherein the diluent further comprises water.

11. The method according to claim 7 wherein the ethanol and the carbon disulfide are introduced into the mixing zone together as a solution of carbon disulfide in ethanol.

12. The method according to claim 11 wherein the ethanol is absolute ethanol.

13. The method according to claim 6 wherein the secondary amine is introduced into the mixing zone as an alkaline aqueous solution.

14. The method according to claim 6 wherein the inert gas is nitrogen or argon gas.

15. The method according to claim 6 wherein the method is performed under sterile conditions.

16. The method according to claim 6 wherein the secondary amine has the formula $R_1R_2NH$, wherein each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate molecules, thereby linking said molecules together so as to form a bis(dithiocarbamate) species.

17. The method according to claim 16 wherein each of $R_1$ and $R_2$ is a $C_1$ up to $C_{12}$ alkyl, substituted alkyl, alkenyl, substituted alkenyl, alkynyl or substituted alkynyl, wherein the substituents are selected from carboxyl, dithiocarbamoyl, —C(O)H, oxyacyl, phenol, phenoxy, pyridinyl, pyrrolidinyl, amino, amido, hydroxy, nitro or sulfuryl.

18. The method according to claim 16 wherein:
   $R_1$ is a $C_2$ up to $C_8$ alkyl or substituted alkyl, wherein the substituents are selected from carboxyl, dithiocarbamoyl, acetyl, pyridinyl, pyrrolidinyl, amino, amido, hydroxy or nitro, and
   $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$.

19. The method according to claim 16 wherein $R_1$ is a $C_2$ up to $C_8$ alkyl or substituted alkyl, wherein the substituents are selected from carboxyl, dithiocarbamoyl, acetyl, amido or hydroxy, and $R_2$ is a $C_1$ up to $C_4$ alkyl or substituted alkyl.

20. The method according to claim 6 further comprising washing the precipitated dithiocarbamate with ethanol having an ethanol content in the range from about 70% ethanol to absolute ethanol.

21. The method according to claim 20 wherein during the washing the ethanol content is increased from about 70% ethanol to absolute ethanol.

22. The method according to claim 6 wherein the precipitated dithiocarbamate has an average major dimension in the size range from about 100 μm to about 1 cm.

23. The method according to claim 6 wherein the inert gas is introduced into the mixing zone at a flow rate from about 0.1 liters to about 300 liters per minute.

24. The method according to claim 23 wherein the inert gas is introduced into the mixing zone at a flow rate from about 30 liters to about 100 liters per minute.

25. The method according to claim 11 wherein the solution is introduced at a flow rate of from about 0.1 liter to about 50 liters per minute.

26. The method according to claim 11 wherein the solution is introduced at a flow rate of from about 1.0 liter to about 20 liters per minute.

27. The method according to claim 6 wherein the mixing zone is substantially closed.

28. The method according to claim 6 wherein the contacting is by a method selected from the group consisting of mixing, stirring, centrifugation, and sparging.

29. The method according to claim 28 wherein the contacting is by centrifugation.

30. The method according to claim 28 wherein the contacting is by stirring with a stirring device.

31. The method according to claim 30 wherein the speed of the stirring device is from about 10 rpm to about 200 rpm.

32. The method according to claim 31 wherein the stirring device is magnetically driven.

33. The method according to claim 30 wherein the stirring device is mechanically driven.

34. The method according to claim 6 wherein the mixture is cooled to a temperature of from about minus 10° C. to about 20° C. at atmospheric pressure.

35. The method according to claim 6 wherein the conditions suitable for precipitating the dithiocarbamate comprise reduced pressure.

36. The method according to claim 6 wherein the separating includes passage through a filter, a screen, or a combination thereof.

37. The method according to claim 36 wherein the filter has a pore size i n the range from about 0.1 μm to about 50 μm.

38. The method according to claim 36 wherein the filter has a pore size in the range from about 10 μm to about 50 μm.

39. The method according to claim 36 wherein the filter has a pore size in the range from about 10 μm to about 20 μm.

40. The method according to claim 6 wherein the method is a batch process.

41. The method according to claim 6 wherein the method is a continuous process.

42. The method according to claim 6 further comprising:
   vigorously stirring a solution of the precipitated dithiocarbamate in pharmaceutical-grade water in a mixing zone, while adding pharmaceutical grade ethanol thereto under conditions suitable for forming a suspension containing a finely-divided dithiocarbamate precipitate therein, and
   separating the finely divided dithiocarbamate precipitate from the suspension, wherein the finely divided dithiocarbamate precipitate is substantially methanol-free.

43. The method according to claim 42 further comprising washing the finely divided dithiocarbamate precipitate with methanol-free ethanol having an ethanol content in the range from about 70% ethanol to absolute ethanol.

44. A method for producing substantially methanol-free pharmaceutical-grade dithiocarbamate particulate, said method comprising:
   vigorously stirring a solution of dithiocarbamate in pharmaceutical grade water, while adding pharmaceutical grade ethanol thereto under conditions suitable for forming a suspension containing a finely-divided dithiocarbamate precipitate therein, and
   separating the dithiocarbamate precipitate from the suspension at reduced pressure, wherein the dithiocarbamate precipitate is substantially methanol-free.

45. The method according to claim 44 wherein the dithiocarbamate feed has the structure (I) as follows:

$$[R_1R_2N\text{—}C(S)\text{—}S^-]_xM \qquad (I)$$

wherein:
   each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ can cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, x is 1 or 2 and M is a suitable counterion.

46. The method according to claim 45 wherein each of $R_1$ and $R_2$ is a $C_1$ up to $C_{12}$ alkyl, substituted alkyl, alkenyl, substituted alkenyl, alkynyl or substituted alkynyl, wherein the substituents are selected from carboxyl, dithiocarbamoyl, —C(O)H, oxyacyl, phenol, phenoxy, pyridinyl, pyrrolidinyl, amino, amido, hydroxy, nitro or sulfuryl.

47. The method according to claim 45 wherein $R_1$ is a $C_2$ up to $C_8$ alkyl or substituted alkyl, wherein the substituents are selected from carboxyl, dithiocarbamoyl, acetyl, pyridinyl, pyrrolidinyl, amino, amido, hydroxy or nitro, and $R_2$ is selected from a $C_1$ up to $C_6$ alkyl or substituted alkyl, or $R_2$ can cooperate with $R_1$ to form a 5-, 6- or 7-membered ring including N, $R_2$ and $R_1$.

48. The method according to claim 45 wherein $R_1$ is a $C_2$ up to $C_8$ alkyl or substituted alkyl, wherein the substituents are selected from carboxyl, dithiocarbamoyl, acetyl, amido or hydroxy, and $R_2$ is a $C_1$ up to $C_4$ alkyl or substituted alkyl.

49. The method according to claim 45 wherein the ethanol is absolute ethanol.

50. The method according to claim 44 further comprising washing the finely divided dithiocarbamate precipitate with methanol-free ethanol having an ethanol content in the range from about 70% ethanol to absolute ethanol.

51. The method according to claim 44 wherein the separating is carried out in a separation zone and the method further comprises introducing an inert gas into the separation zone.

52. The method according to claim 51 wherein the inert gas is introduced through a sterile filter.

53. The method according to claim 51 wherein the inert gas is nitrogen or argon.

54. The method according to claim 53 further comprising passing the solution into the mixing zone through a sterilizing filter.

55. The method according to claim 44 wherein the method is conducted under sterile conditions, thereby producing sterile dithiocarbamate particulate.

56. The method according to claim 44 wherein the method is a batch process.

57. The method according to claim 44 wherein the method is a continuous process.

58. A method for producing substantially methanol-free sterile dithiocarbamate, said method comprising:

sterilizing a solution of dithiocarbamate in pharmaceutical-grade water, vigorously stirring the solution in a sterile mixing zone while adding thereto sterile pharmaceutical grade, methanol-free ethanol under conditions suitable for forming a suspension containing a finely-divided dithiocarbamate precipitate therein, and separating the dithiocarbamate precipitate from the suspension at reduced pressure and under sterile conditions, wherein the dithiocarbamate precipitate is substantially methanol-free.

59. The method according to claim 58 wherein the separating involves passage of the precipitate through a separation zone.

60. The method according to claim 58 further comprising washing the separated precipitate with a sterile wash methanol-free ethanol having an ethanol content in the range from about 70% ethanol to absolute ethanol.

61. The method according to claim 60 wherein during the washing the ethanol content in the wash ethanol is increased from about 70% ethanol to absolute ethanol.

62. The method according to claim 60 wherein each of the solution of dithiocarbamate and the ethanol are sterilized by passage into the mixing zone through a sterilizing filter.

63. The method according to claim 62 wherein the wash ethanol is sterilized by passage through a sterilizing filter.

64. The method according to claim 58 wherein the separating includes passage through a filter, a screen, or a combination thereof.

65. The method according to claim 58 further comprising drying the separated precipitate to constant weight.

66. The method according to claim 65 wherein the drying comprises passage of a sterile inert gas over the separated precipitate.

67. The method according to claim 66 wherein the inert gas is made sterile by passage through a sterilizing filter.

68. The method according to claim 58 further comprising placing a unit dose of the precipitated dithiocarbamate into each of a plurality of vials under sterile conditions.

69. A sterile, methanol-free pharmaceutical-grade dithiocarbamate produced by the method of claim 5.

70. A sterile, methanol-free pharmaceutical-grade dithiocarbamate produced by the method of claim 15.

71. A sterile, methanol-free pharmaceutical-grade dithiocarbamate produced by the method of claim 55.

72. A sterile, methanol-free pharmaceutical-grade dithiocarbamate produced by the method of claim 58.

* * * * *

UNITED STATES PATENT AND TRADEMARK OFFICE
CERTIFICATE OF CORRECTION

PATENT NO. : 6,124,349
DATED : September 26, 2000
INVENTOR(S) : Vassilev et al.

Page 1 of 1

It is certified that error appears in the above-identified patent and that said Letters Patent is hereby corrected as shown below:

Column 11,
Line 63, delete "substantially"

Column 12,
Lines 9, 20 and 32, delete "substantially"

Column 13,
Line 46, delete "substantially"

Column 14,
Line 2, delete "i n" and substitute -- in --
Line 23, delete "substantially"
Lines 29 and 39, delete "substantially"

Column 15,
Line 43, delete "substantially"

Column 16,
Line 9, delete "substantially"

Signed and Sealed this

Twenty-eighth Day of January, 2003

JAMES E. ROGAN
*Director of the United States Patent and Trademark Office*